(12) United States Patent
Haras

(10) Patent No.: US 7,465,090 B2
(45) Date of Patent: Dec. 16, 2008

(54) MEDICAL IMAGING INSTALLATION AND METHOD FOR SUCH AN INSTALLATION

(75) Inventor: Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/699,472

(22) Filed: Jan. 30, 2007

(65) Prior Publication Data

US 2007/0189456 A1 Aug. 16, 2007

(30) Foreign Application Priority Data

Jan. 31, 2006 (DE) .................. 10 2006 004 692

(51) Int. Cl.
*A61B 6/08* (2006.01)
(52) U.S. Cl. ..................... 378/206; 378/98.5
(58) Field of Classification Search .............. 378/98, 378/98.2, 98.3, 98.5, 204–206
See application file for complete search history.

(56) References Cited

U.S. PATENT DOCUMENTS

| 4,117,337 | A | 9/1978 | Staats ..................... 250/445 T |
| 5,707,360 | A | 1/1998 | Röckseisen ................. 604/116 |
| 5,792,147 | A * | 8/1998 | Evans et al. ................. 606/130 |
| 6,064,904 | A | 5/2000 | Yanof et al. ................. 600/414 |
| 6,473,489 | B2 | 10/2002 | Bani-Hashemi et al. ....... 378/63 |

FOREIGN PATENT DOCUMENTS

| DE | 295 02 525 | 6/1995 |
| DE | 100 49 103 | 1/2005 |
| DE | 698 26 421 | 9/2005 |

OTHER PUBLICATIONS

German Office Action (dated Jan. 16, 2007) for counterpart German Patent Application 10 2006 004 692.7.

* cited by examiner

*Primary Examiner*—Jurie Yun
(74) *Attorney, Agent, or Firm*—Harness, Dickey & Pierce, P.L.C.

(57) ABSTRACT

A medical imaging installation and a method for a medical imaging installation are disclosed for defining a specific position on the surface of an object. In at least one embodiment, the installation has a support apparatus for an object, a device for recording measured data from the object in order to produce an image of the object, a unit for displaying an image obtained from the object, and a device, arranged on the installation in a defined fashion, for projecting a light pattern onto the surface of the object. The light pattern is inserted appropriately into the displayed image of the object in order to define a specific position on the surface of the object.

28 Claims, 3 Drawing Sheets

FIG 5

Spiral scan or sequence scan for planning the surgery on the patient

Selection and display of a tomogram, and definition of the puncture site

Insertion of the light grid into the tomogram, and determination of the position of the puncture site in the inserted light grid

Determination of the position, belonging to the tomogram, of the support plate, and setting of the position of the support plate

Actual projection of the light grid onto the patient's body surface in accordance with the selected tomogram

Determination of the puncture site in the actually projected light grid on the basis of the displayed tomogram with inserted light grid

Application of the biopsy needle and beginning of the surgery

MEDICAL IMAGING INSTALLATION AND METHOD FOR SUCH AN INSTALLATION

PRIORITY STATEMENT

The present application hereby claims priority under 35 U.S.C. §119 on German patent application number DE 10 2005 004 692.7 filed Jan. 31, 2006, the entire contents of which is hereby incorporated herein by reference.

FIELD

Embodiments of the invention generally relate to a medical imaging installation. For example, they may relate to one having a support apparatus for an object, a device for recording measured data from the object in order to produce an image of the object, a unit for displaying an image obtained from the object, and a device, arranged on the installation, for projecting a light pattern onto the surface of the object. Embodiments of the invention also generally relate to a method for such a medical imaging installation for defining a specific position on the surface of an object.

BACKGROUND

A medical imaging installation in the form of an x-ray computed tomography installation is disclosed, for example, in U.S. Pat. No. 4,117,337. Two lasers are used to project in each case a cruciform light pattern onto the body surface of a patient in order, for example, to display the position of a scanning plane of the x-ray computed tomography installation.

In the field of medicine, the treatment of a patient, for example, frequently also requires a specific position to be marked on the patient's body surface. Such a procedure is performed, for example, when preparing for surgery on the patient, recorded images of the patient being used in order to define the specific position. Thus, it is currently customary, for example when using an x-ray computed tomography installation, to undertake a so-called planning scan of the patient in which images of the patient are obtained in sequence mode or spiral mode in order to secure an impression of the topographic conditions and to define the surgery position and, if appropriate, the surgery axis for the operation. Upon conclusion of the planning, the surgery position defined with the aid of the images, which can, for example, be a puncture site for a biopsy needle, is sought out on the patient and, if appropriate, the puncture angle for the surgery is defined.

In order to find the puncture site on the patient's body surface, when use has been made of an x-ray computed tomography installation in recording the images of the patient, the latter, who is supported on the support apparatus of the computed tomography installation, is adjusted together with the support apparatus in such a way that the slice position selected during planning is approached and marked with the aid of a so-called laser light sight that is arranged on the computed tomography installation. In what follows, an x-ray positive marking is applied at the site on the patient's body surface at which the correct position of the puncture site is thought to be from the planning. Finally, a control scan is used to check whether the site has been correctly marked. If the site has been missed, the marking must be corrected, and a further control scan is required.

There can be a need in some cases for a number of control scans in order to find the correct puncture site on the patient's body surface. In unfavorable cases, the patient is thus exposed repeatedly to x-radiation solely in order to find the surgery position, and this is undesirable. Moreover, this procedure can make commands on a relatively long time for preparing the surgery, and this has a negative effect on the workflow in the medical facilities. Otherwise, the surgery itself is generally performed under x-ray control, that is to say during surgery images of the patient are obtained at specific points in time in order to be able to observe the progress of the surgery.

SUMMARY

In at least one embodiment of the invention, a medical imaging installation and/or a method is specified for a medical imaging installation of the type mentioned at the beginning in such a way that finding a specific position on the surface of an object is simplified.

According to at least one embodiment of the invention, a medical imaging installation that has a support apparatus for an object and a device for recording measured data from the object is used to produce at least one image of the object that is displayed with the aid of a display unit. Furthermore, the medical imaging installation has a device for projecting a light pattern onto the surface of the object in order to find the specific position on the surface of the object.

According to at least one embodiment of the invention, for the purpose of defining a specific position on the surface of the object the light pattern, which can be produced in real terms per se with the aid of the device for projecting a light pattern, is then inserted in an appropriate way into a selected, displayed image of the object. The selected, displayed image of the object can now be used to define a specific position on the surface of the object that, in the case of surgery on a patient, is a puncture site for a biopsy needle, for example. The additional insertion of the light pattern that appropriately simulates the real light pattern into the selected, displayed image of the object is an aid to orientation and, finally, enables the marking of the specific position undertaken in the selected, displayed image to be transferred in an appropriate way onto the surface of the object through orientation on the light pattern actually projected onto the surface of the object.

By contrast with the prior art, this requires no additional recorded images of the object for control purposes in order to establish whether the marking of the specific position undertaken in the image corresponds to the actually marked specific position. Thus, at least one embodiment of the invention reduces the radiation burden on the patient and the user, since control scans are rendered unnecessary. Moreover, the entire duration of a radiological operation can be shortened, since the puncture site can be found more quickly. In addition, the lying time, which is unpleasant for the patient, can be shortened, while the patient throughput can also be raised.

Once this specific position in the selected image has been defined, preferably with the aid of the light pattern inserted into the image, the support apparatus with the object can be adjusted in such a way that with the aid of the device for projecting the light pattern, the latter is projected in real terms onto the surface of the object in such a way that the real projection corresponds substantially to the projection of the light pattern inserted in the image. This adjustment of the support apparatus is possible without a problem because the coordinate system of the images produced with the aid of the medical imaging installation, and thus also of the displayed, selected image is uniquely linked to the coordinate system of the medical imaging installation and, in addition, the device for projecting the light pattern is arranged in a defined way on the medical imaging installation.

Consequently, by adjusting the support apparatus provided with the object it is possible for the actual situation to be adapted to the situation displayed in the image or to be made to conform therewith such that the real projection of the light pattern onto the surface of the object corresponds to the projection, displayed in the image, of the light pattern onto the surface of the object.

According to one embodiment of the invention, the medical imaging installation has a computing device that determines the adjusting path of the support apparatus provided with the object on the basis of the definition, undertaken in the selected, displayed image, of the specific position, and prompts the appropriate adjustment of the support apparatus. The computing device preferably serves also for pictorial display with the aid of the display unit, conventional input means such as a computer mouse or a keyboard being connected to the computing device, which mouse or keyboard can be used by the user inter alia to use to enter the definition of the specific position on the surface of the object into the selected, displayed image of the object.

According to one embodiment of the invention, the light pattern is a grid having a number of preferably rectangular or square grid elements that form, for example, a linear, rectangular or square overall grid. A grid is particularly suitable as an aid to orientation for defining the specific position on the surface of an object.

According to example embodiments of the invention, the light pattern comprises a coding, the latter possibly being lines of different thickness, numbers and/or colors. The codings again facilitate transferring the marking of the specific position undertaken in the image in real terms onto the surface of the object.

According to a further embodiment of the invention, the insertion of the light pattern into the selected, displayed image of the object is performed in such a way that the display of the light pattern with respect to size and orientation is adapted to the display of the object, such that the specific position defined with the aid of the image can in real terms easily be transferred onto the surface of the object.

Variants of embodiments of the invention provide that the projection of the light pattern onto the surface of the object is performed with the aid of parallel light beams or fan-shaped light beams emanating from a focus, according to one embodiment of the invention the device for projecting a light pattern onto the surface of the object comprising at least one laser emitting visible light, preferably a helium neon laser. The laser is in this case assigned an appropriate optics such that the light pattern can be projected onto the surface of the object.

The medical imaging installation is preferably an x-ray computed tomography installation, the device for projecting the light pattern onto the surface of the object preferably being arranged in defined fashion on the stationary part of the gantry of the x-ray computed tomography installation, such that, as already mentioned above, there is a unique relationship between the coordinate system of the selected, displayed image and the coordinate system of the device for projecting the light pattern, and therefore the support apparatus with the object can be uniquely adjusted in such a way that the projection, displayed in the image, of the light pattern onto the surface of the object corresponds to the real projection of the light pattern onto the surface of the object.

At least one embodiment of the invention is preferably used to define a specific position on a patient's body surface for a medical operation, this being understood as insertion of a medical instrument, for example, a biopsy needle, into a patient's body.

BRIEF DESCRIPTION OF THE DRAWINGS

An example embodiment of the invention is illustrated in the attached schematics, in which:

FIG. 5 shows a flowchart for determining the puncture site of a medical instrument on the patient's body surface.

DETAILED DESCRIPTION OF THE EXAMPLE EMBODIMENTS

Figure 1:
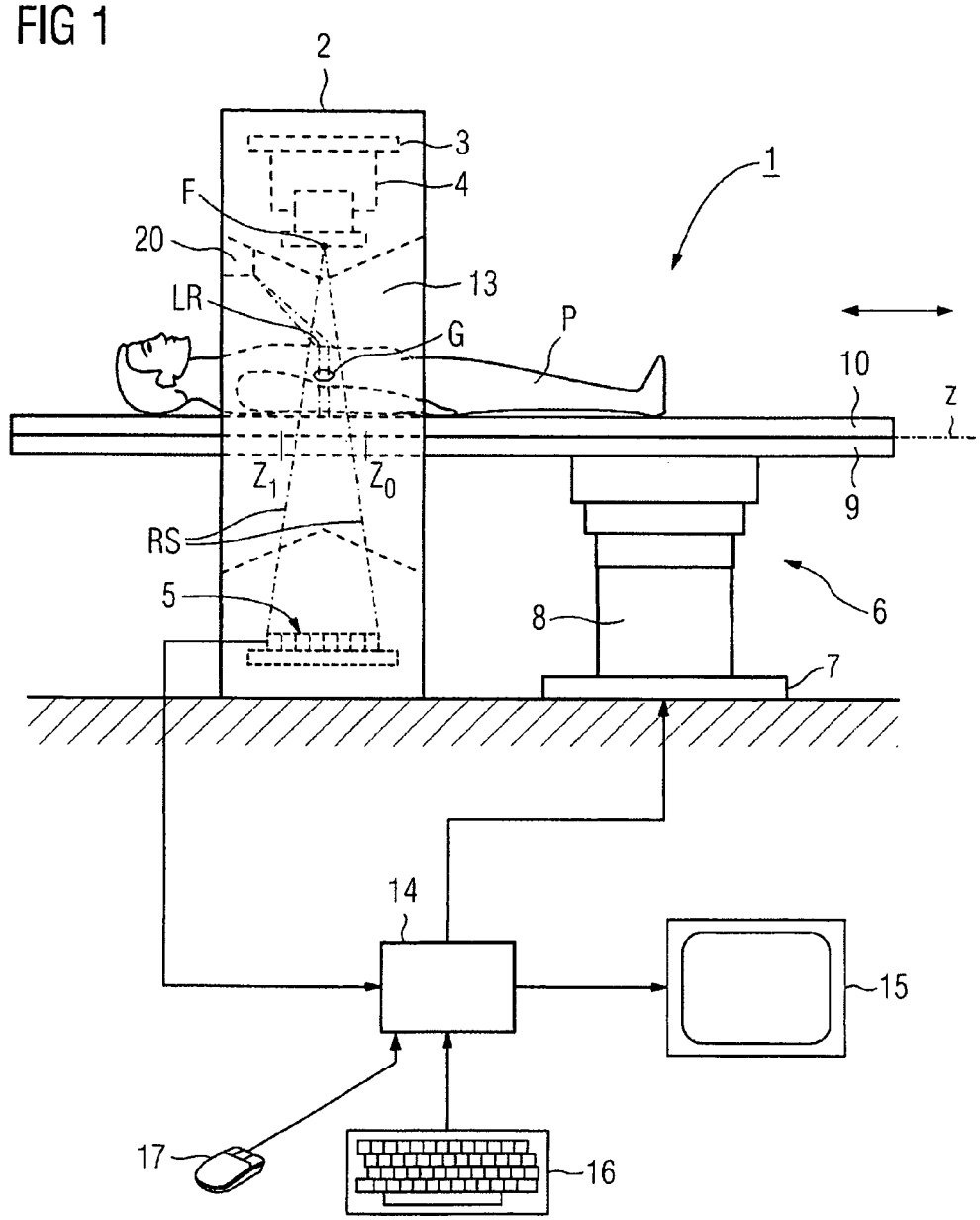
FIG. 1 shows an x-ray computed tomography installation.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 is a schematic, partially a block diagram, of a medical imaging installation in the form of an x-ray computed tomography installation 1. The x-ray computed tomography installation 1 includes a gantry having a stationary part 2 and a rotary frame 3 that is arranged in the stationary part 2 and can rotate about a system axis Z of the x-ray computed tomography installation 1. Arranged on the rotary frame 3 is an x-ray source 4 from whose focus F there emanates an x-ray beam RS that is shaped like a fan or a pyramid, for example, with the aid of diaphragms that are not illustrated in FIG. 1 but are known per se. Arranged opposite the x-ray source 4 on the rotary frame 3 in the case of the present example embodiment is a multirow x-ray detector 5.

The x-ray computed tomography installation 1 further includes a patient support table 6 having a pedestal 7, a lifting column 8, a base part 9 and a support plate 10. The support plate 10 can be adjusted in the direction of the system axis Z of the x-ray computed tomography installation 1 on rails that are not shown in more detail. The adjustment of the support plate 10 relative to the base part 9 is performed in the case of the present example embodiment in a motorized fashion by way of electric motors that are not illustrated physically but are known per se.

Supported in the case of the present example embodiment on the support plate 10 is a patient P on whom it is intended to carry out a medical operation, the aim being for a medical instrument, in the present case a biopsy needle (not illustrated in more detail) for extracting a sample from a tissue G in the body interior of the patient P, to be inserted into the patient P. In order to be able to guide the biopsy needle in an accurately targeted fashion into the tissue G, the x-ray computed tomography installation 1 is used to obtain images from the body interior of the patient P such that the puncture site for the biopsy needle on the body surface of patient P can be defined with the aid of the image information from the patient P. In order to obtain the information from the patient P supported on the support plate 10, in particular from patient P's body region containing the tissue G, the support plate 10 is moved with the patient P into or through the opening 13 in the gantry 2.

Irrespective of whether the patient P is being examined in sequence mode or in spiral mode with continuous table feed of the x-ray computed tomography installation 1, x-radiation RS emanating from the focus F of the x-ray source 4 penetrates the body of the patient P to be examined and strikes the x-ray detector 5. In this case, the rotary frame 3 rotates with the x-ray source 4 and the x-ray detector 5 about the system axis Z of the x-ray computed tomography installation 1 and about the patient P, x-ray projection images of the patient P being obtained from different projection directions.

With each x-ray projection image, x-radiation that has passed through the patient P and been attenuated by the passage through the patient strikes the x-ray detector 5. The x-ray detector 5 in this case generates signals corresponding to the intensity of the impinging x-radiation. Consequently, a computing device 14 uses the signals determined with the aid of the x-ray detector 5 to calculate in a way known per se one or more two- or three-dimensional images of patient P's recorded body region, and these can be displayed on the visual display unit 15. Again, an input device, such as the keyboard 16 and the computer mouse 17 illustrated by way of example in FIG. 1, are present for operating the x-ray computed tomography installation 1.

Moreover, a device for projecting a light pattern onto the body surface of patient P is arranged on the stationary part 2 of the gantry in a defined way relative to the measurement system, having the x-ray source 4 and the x-ray detector 5, of the x-ray computed tomography installation 1 such that there is a unique relationship between a coordinate system of the measurement system and a coordinate system of the device for projecting the light pattern. In the case of the present example embodiment, the device for projecting a light pattern is a helium neon laser device 20 having a suitable optics. The laser device 20 is arranged on the stationary part 2 of the gantry in such a way that the recording of x-ray projections is not impeded.

In the case of the present example embodiment, in order to define the surgery position and/or the puncture site for the biopsy needle on patient P's body surface a number of two-dimensional tomograms and/or sectional images are reconstructed from patient P's body region relevant for the purpose which, as already mentioned, are displayed on the visual display unit 15. The recording of the x-ray projections of the relevant patient P's body region that are required therefore begins in this case at a starting position $z_0$ and ends at a final position $z_1$ of the support plate 10 of the patient P relative to the base part 9 of the patient support table 6 or to the rotary frame 3, which is stationary in the Z direction, and thus to the imaging plane. Thus, when tomograms of a specific slice width of the relevant patient P's body region are subsequently reconstructed, it is possible on the basis of the reconstruction parameters used to assign each of these tomograms a specific Z position of the support plate 10 or of the patient P relative to the imaging plane or to the base part 9 if the patient P experiences no change in position relative on the support plate 10 itself.

Figure 2:
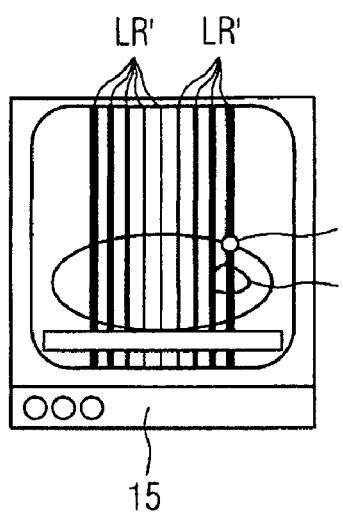
FIG. 2 shows the insertion of a light grid into a tomogram of a patient, and the corresponding real projection of the light grid onto the patient's body surface on the x-ray computed tomography installation.
Figure 2:
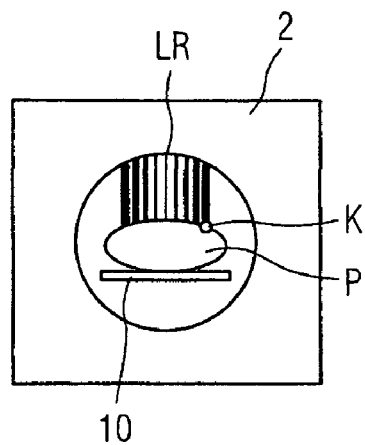

In order to select a tomogram for defining the puncture site, a doctor can, for example, use the input device to leaf through the various reconstructed tomograms of the patient P, and display that tomogram on the visual display unit 15 that is best suited for defining the puncture site of the biopsy needle on patient P's body surface. As is illustrated in FIG. 2, the doctor can now use the displayed tomogram selected on the visual display unit 15 to mark the puncture site for the biopsy needle by way of an appropriate marking K', a circle in the present case.

In order to be able to transfer the circular marking K' undertaken in the selected, displayed tomogram onto patient P's body surface, according to an embodiment of the invention a light grid LR' is now inserted into the selected, displayed tomogram or superposed on the tomogram, and the position of the puncture site is determined in the light grid LR' inserted into the tomogram. The insertion of the light grid LR' is illustrated by way of example in FIG. 2. The insertion of the light grid LR' is in this case adapted to the so-called field of view (FOV) of the displayed, selected tomogram, that is to say the size and the alignment of the display of the light grid LR' are adapted to the display of the patient P. It is preferred to insert into the selected, displayed tomogram a linear light grid LR, shown in FIG. 3, that has one or more codings.

Figure 3:
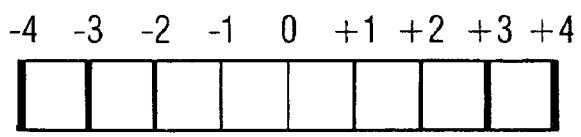
FIG. 3 shows an example of a light grid provided with codings.

As illustrated in FIG. 3, the codings can be numbers that, if appropriate, are provided with signs, lines or grid lines of different thickness, and/or colored codings (not shown specifically in FIG. 3). The codings can be inserted into the selected, displayed tomogram of the patient P simply on their own, or else in any desired combination together with the light grid LR'. Since there is a unique relationship between the coordinate system of the selected, displayed tomogram and the coordinate system of the x-ray computed tomography installation 1 and thus also in relation to the laser device 20, the computing device 14 can determine the position, belonging to the selected, displayed tomogram of the patient P, of the support plate 10 relative to the measurement system of the x-ray computed tomography installation 1 and can, by driving the electric motors that effect the displacement of the support plate 10, position the support plate 10 in such a way that the light grid LR is projected in real terms onto the patient P body surface with the aid of the laser device 20 in such a way that the real projection of the light grid LR corresponds substantially to the projection, inserted in the image, of the light grid LR'.

Here, the computing device 14 has a corresponding software for setting the support plate 10. This situation is illustrated in FIGS. 1 and 2, with the projection of the light grid LR onto the patient P body surface with the aid of the laser device 20 corresponding to the projection, inserted in the selected tomogram, of the light grid LR'. The light grids LR and LR' correspond to one another in this case. It is possible in this way for the doctor to orient himself on the light grid LR' inserted into the displayed, selected tomogram, and to define and mark the puncture site on the patient P's body surface with the aid of the light grid LR actually projected onto the patient P's body surface, and this can be performed, for example, by counting of grid elements. Thus, the doctor transfers the puncture site selected with the aid of the selected, displayed tomogram onto the actual situation, that is to say onto the patient P body surface. The puncture site for the surgery is thereby defined such that the biopsy needle can be applied and the surgery can be undertaken on the patient. If appropriate, it is still necessary here for the doctor to select the puncture angle appropriately with the aid of the displayed image information.

In the case of the present example embodiment, the light grid LR is substantially projected into the imaging plane of the x-ray computed tomography installation 1. This is the general case, since the subsequent surgery is mostly performed under x-ray control, that is to say the patient P or the support plate 10 is already suitably aligned in relation to the measurement system when transferring the marking onto the patient P's body surface for the subsequent surgery. If desired, however, the light grid need not be projected in such a way. However, the projection can also be situated entirely outside the imaging plane.

Figure 4:
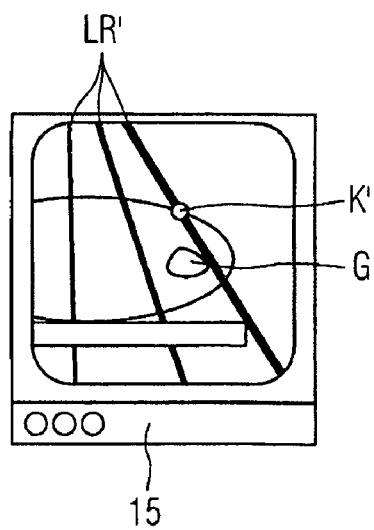
FIG. 4 shows an insertion, alternative to FIG. 2, of a light grid, and the actual production of a light grid.
Figure 4:
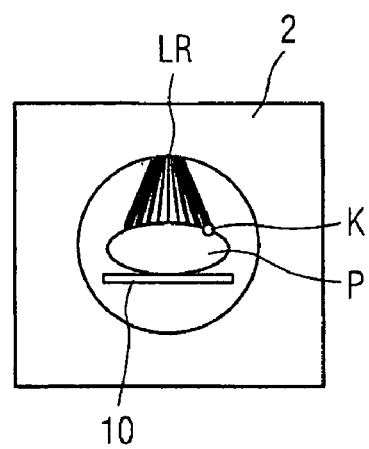

As indicated in FIG. 4, the light grid can also be produced with fan-shaped light beams as an alternative to the insertion, shown in FIG. 2, of the light grid with the aid of parallel light beams. Another suitable optics is to be provided for this purpose on the laser device 20. Otherwise, it is also possible to use a number of lasers for producing the light grid, it being possible to implement the color codings when selecting different lasers, that is to say lasers that emit light of different wavelength.

The sequence of the method for determining the puncture site of the biopsy needle is shown once again in the flow chart of FIG. 5. Individual method steps can also be exchanged in this case.

Again, the medical imaging installation need not necessarily be an x-ray computed tomography installation. Rather, other medical imaging installations, for example magnetic resonance installations, C-arc x-ray installations or ultrasound installations, are suitable for obtaining the image information from the patient P.

The light pattern need not necessarily be implemented in the form of a grid. Rather, other light patterns are also suitable which permit a position to be transferred onto a surface from a displayed image. The light pattern need not necessarily have a coding in this case.

The light pattern need not necessarily be inserted into a tomogram or sectional image. Rather, the light pattern can also be inserted into a fluoroscopic image or into a 3D image of an object in order to define a specific position on the surface of the object.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical imaging installation comprising:
a support plate for an object;
a device to record measured data from the object to produce an image of the object;
a unit to display an image obtained from the object; and
a device, arranged on the installation in a defined fashion, to project an actual light pattern onto the surface of the object, the actual light pattern defining a specific position on the surface of the object and corresponding to a virtual light pattern inserted into a selected portion of the displayed image of the object.

2. The medical imaging installation as claimed in claim 1, wherein the specific position on the surface of the object corresponds to a specific position on the selected portion of the displayed image, and the support plate with the object is adjustable in such a way that the actual light pattern corresponds to the inserted virtual light pattern.

3. The medical imaging installation as claimed in claim 2, further comprising:
a computing device to determine an adjusting path of the support plate based on the specific position on the selected portion of the displayed image and to prompt a determined adjustment of the support plate.

4. The medical imaging installation as claimed in claim 1, wherein the virtual light pattern is a grid.

5. The medical imaging installation as claimed in claim 1, wherein the virtual light pattern includes a coding.

6. The medical imaging installation as claimed in claim 5, wherein the coding is performed by at least one of lines of different thickness, numbers and colors.

7. The medical imaging installation as claimed in claim 1, wherein the insertion of the virtual light pattern into the selected portion of the displayed image is performed in such a way that the virtual light pattern is adapted to the selected portion of the displayed image.

8. The medical imaging installation as claimed in claim 1, wherein the projection of the actual light pattern onto the surface of the object is performed with at least one of parallel and fan-shaped light beams.

9. The medical imaging installation as claimed in claim 1, wherein the device to project the actual light pattern onto the surface of the object comprises at least one laser emitting visible light.

10. The medical imaging installation as claimed in claim 1, wherein the medical imaging installation is an x-ray computed tomography installation.

11. The medical imaging installation as claimed in claim 10, wherein the device to project the actual light pattern onto the surface of the object is arranged on the stationary part of a gantry of the x-ray computed tomography installation.

12. A method for a medical imaging installation for defining a specffic position on the surface of an object, comprising:
producing a plurality of tomograms in a z-range of the object, the z-range including a body-part to be punctured, the plurality of tomograms being produced with the aid of a device for recording measured data of the medical imaging installation from the object arranged on a support plate, the support plate being adjustable in a z-direction;
selecting a tomogram in which the body-part is displayed;
displaying the selected tomogram with the aid of a display unit;
inserting a virtual light grid into the displayed tomogram;
determining a virtual surface position of a virtual puncture site in the selected tomogram;
positioning the support plate appropriately based on the selected tomogram;
projecting an actual light grid onto the surface of the object, the actual light grid corresponding to the virtual light grid; and
locating an actual puncture site on the surface of the object, the actual puncture site corresponding to the virtual puncture site on the selected tomogram.

13. The method as claimed in claim 12, wherein a computing device determines an adjusting path of the support plate based on the determined virtual surface position, and prompts the appropriate adjustment of the support plate.

14. The method as claimed in claim 12, wherein the virtual light grid comprises a coding.

15. The method as claimed in claim 14, wherein the coding is performed by at least one of lines of different thickness, numbers and colors.

16. The method as claimed in claim 12, wherein the insertion of the virtual light grid into the displayed tomogram is performed in such a way that the virtual light grid is adapted to the displayed tomogram.

17. The method as claimed in claim 12, wherein the projection of the actual light grid onto the surface of the object is performed with at least one of parallel and fan-shaped light beams.

18. The method as claimed in claim 12, wherein a device to project the actual light grid onto the surface of the object comprises at least one laser emitting visible light.

19. The method as claimed in claim 18, wherein the medical imaging installation is an x-ray computed tomography installation.

20. The method as claimed in claim 19, wherein the device to project the actual light grid onto the surface of the object is arranged on the stationary part of a gantry of the x-ray computed tomography installation.

21. The method as claimed in claim 12, wherein the method is provided for defining a specific medical intervention position.

22. A medical imaging installation comprising:
a support plate for an object;
means for recording measured data from the object to produce an image of the object;
means for displaying an image obtained from the object; and
means, arranged on the installation in a defined fashion, for projecting an actual light pattern onto the surface of the object, the actual light pattern defining a specific position on the surface of the object and corresponding to a virtual light pattern inserted into a selected portion of the displayed image of the object.

23. The medical imaging installation as claimed in claim 22, wherein the specific position on the surface of the object corresponds to a specific position on the selected portion of the displayed image, the support plate with the object being adjustable in such a way that the actual light pattern corresponds substantially to the virtual light pattern inserted in the selected portion of the displayed image.

24. The medical imaging installation as claimed in claim 23, further comprising:
means for determining an adjusting path of the support plate based on the specific position in the selected portion of the displayed image and for prompting a determined adjustment of the support plate.

25. A method for a medical imaging installation for defining a specific position on the surface of an object, comprising:
recording measured data from the object on a support plate to produce images of the object;
displaying an image obtained from the object; and
projecting an actual light pattern onto the surface of the object, the actual light pattern defining a specific position on the surface of the object and corresponding to a virtual light pattern inserted into a selected portion of the displayed image of the object.

26. The method of claim 25, wherein the selected portion of the image is a tomogram, the method further comprising:
selecting the tomogram containing a body-part to be punctured;
determining a virtual surface position of a virtual puncture site in the selected tomogram;
positioning the support plate based on the selected tomogram; and
locating an actual puncture site on the surface corresponding to the virtual puncture site.

27. A medical imaging installation comprising:
a support plate capable of supporting an object, the support plate being adjustable in a z-direction;
a device to record measured data from the object and to produce a plurality of tomograms in a z-range of the object, the z-range including a body-part to be punctured;
an input device to select one of the plurality of tomograms and to select a virtual puncture site on the selected tomogram, the puncture site being defined by a virtual light grid inserted into the selected tomogram;
a display unit to display the selected tomogram and inserted virtual grid; and
a device, arranged on the installation, to project an actual light grid onto a surface of the object, the actual light grid corresponding to the virtual light grid and defining an actual puncture site on the surface of the object.

28. A medical imaging installation comprising:
a support plate capable of supporting an object, the support plate being adjustable in a z-direction;
means for producing a plurality of tomograms in a z-range of the object, the z-range including a body-part to be punctured;
means for selecting a tomogram in which the body-part is displayed;
means for displaying the selected tomogram obtained from the object;
means for inserting a virtual light grid into the displayed tomogram of the object to define a virtual puncture site on the surface of the object;
means for determining a virtual surface position of the virtual puncture site in the selected tomogram;

means for positioning the support plate appropriately based on the selected tomogram;

means for projecting an actual light grid onto the surface of the object, the actual light grid corresponding to the virtual light grid; and means for locating an actual puncture site on the surface, the actual puncture site corresponding to the virtual puncture site.

* * * * *